United States Patent [19]

Ramos Martinez

[11] 4,225,980
[45] Oct. 7, 1980

[54] METALLIC CARDIAC VALVE PROSTHESIS

[76] Inventor: Wilson Ramos Martinez, Avda. Generalísimo, 96 - piso 16 Apto. 10, Madrid, Spain

[21] Appl. No.: 964,442

[22] Filed: Nov. 28, 1978

[30] Foreign Application Priority Data

Jan. 7, 1978 [ES] Spain ................................. 465.824

[51] Int. Cl.³ .............................................. A61F 1/22
[52] U.S. Cl. .................................... 3/1.5; 137/527.8
[58] Field of Search ............................ 3/1.5; 137/527.8

[56] References Cited

U.S. PATENT DOCUMENTS

| | | | |
|---|---|---|---|
| 3,445,863 | 5/1969 | Wada | 3/1.5 |
| 3,448,465 | 6/1969 | Pierce et al. | 3/1.5 |
| 3,546,711 | 12/1970 | Bokros | 3/1.5 |
| 3,926,215 | 12/1975 | Macleod | 3/1.5 X |

OTHER PUBLICATIONS

"Artificial Mitral Valves" by J. H. Stuckey, Transactions on Medical Electronics, Mar. 1959, vol. ME6, No. 1.

Primary Examiner—Ronald L. Frinks
Attorney, Agent, or Firm—Wenderoth, Lind & Ponack

[57] ABSTRACT

A metallic cardiac valve prosthesis having an aortic as well as a mitral application, the purpose of which is to obtain an ample, highly physiological and laminar flow of blood, includes a ring, the outer contour of which is circular and the inner contour of which is oval. The interior of the ring is provided with a lenticular plug acting in the same way as the plug of a butterfly valve.

4 Claims, 2 Drawing Figures

METALLIC CARDIAC VALVE PROSTHESIS

BACKGROUND AND SUMMARY OF THE INVENTION

This invention relates to a metallic cardiac valve prosthesis, the main characteristics of which are a reduced profile, and offering two varieties, an aortic and a mitral.

The heretofore existing metallic cardiac valve prosthesis devices present various problems, among which the most important is the system of the flow of blood. The prothesis of this invention overcomes these problems and mainly that of the mentioned flow of blood, obtaining a better yield in cardiac capacity, both for the aortic as well as for the mitral variety. A more physiological flow of blood is obtained which is considerably better than with all the heretofore existing metallic cardiac valve prosthesis devices.

Thus, the prosthesis of this invention includes a ring, the outer contour of which is circular and the inner contour of which is oval. An oval-shaped lenticular plug, constituting the movable element of the valve, is articulately housed in the ring.

The lenticular plug is articulated to the ring by two steps formed opposite to each other in the inner perimeter of the ring, as well as by two pivots which project inwardly of the body of the ring and which are housed in grooves or recesses made in the lenticular plug.

The imaginary axis of articulation of the lenticular plug, established by the mentioned pivots and grooves, is established in the plug in a direction parallel to the minor axis of the plug and off-center of the plug, so that one-third of the surface of the plug in on one side of the axis of articulation and the remaining two-thirds of the surface of the plug is on the other side of the axis of articulation.

BRIEF DESCRIPTION OF THE DRAWINGS

Other features of the invention will be apparent from the following description, taken with the accompanying drawings, wherein.

DETAILED DESCRIPTION OF THE INVENTION

Figure 1:
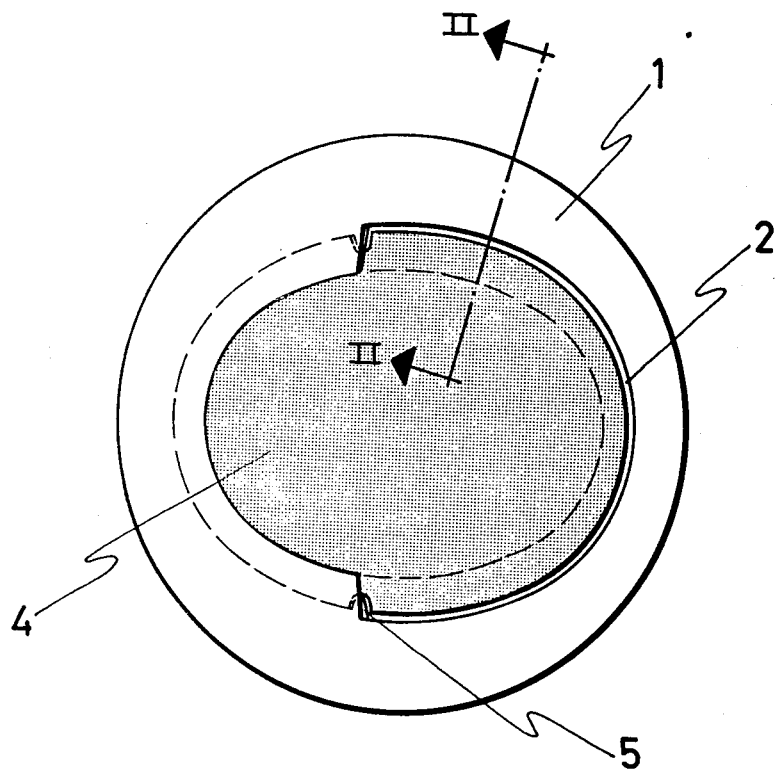
FIG. 1 is a plan view of a metallic cardiac valve prosthesis device according to the invention.
Figure 2:
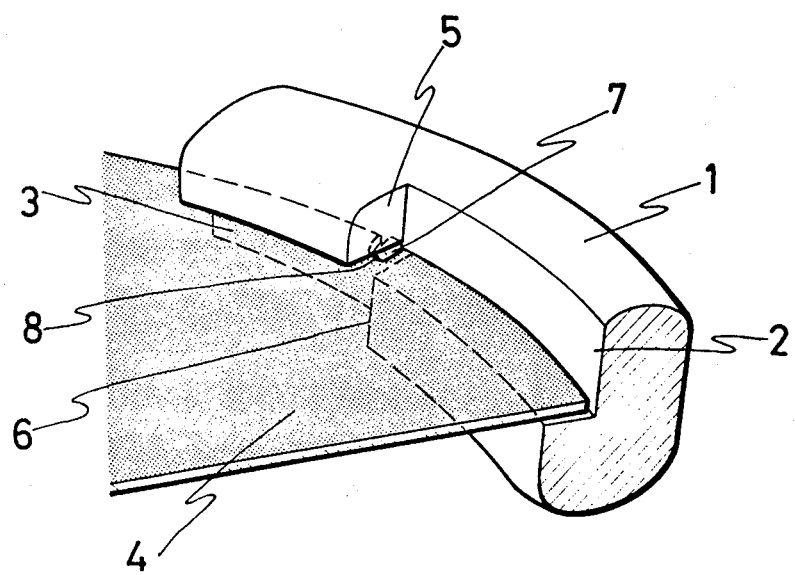
FIG. 2 is a partial sectional perspective view, taken approximately along lines II—II of FIG. 1, of the prosthesis device clearly illustrating the shape of the various component elements thereof in the articulation zone of the lenticular plug.

As seen in the drawings, the prosthesis includes a ring 1, generally rectangular in cross section and the edges of which are pronouncedly rounded. The outer contour of the ring is perfectly circular while its inner contour is oval, as can be seen in FIG. 1. Thus, as is clear, the thickness of the ring is at its maximum in the zones corresponding to the ends of the minor axis of the oval orifice, and the thickness of the ring is progressively reduced towards the zones corresponding to the ends of the major axis of the oval orifice, whereat the thickness is at a minimum.

In the inside of the ring there are two steps 2 and 3 situated opposite to each other, so that one of them opens towards one of the surfaces of the ring while the other opens towards the opposite surface of the ring. The steps 2 and 3 constituting the support plane for the closure of a lenticular plug 4. Thus, the lenticular plug 4 has an oval shape corresponding to that formed by the surfaces of the steps 2 and 3. It is also clear that, for a perfect coupling of the lenticular plug 4 to the steps 2 and 3, the steps should be dephased or defined in planes which are spaced from one another in a magnitude coinciding with the thickness of the plug.

The lenticular plug 4 is mounted to be precisely articulated at the end zones or faces 5 and 6 of the steps 2 and 3. Faces or zones 5 and 6 are sufficiently dephased or circumferentially spaced from each other so as to permit the oscillation of the plug 4 until an angle, the value of which is fixed from 80° to 85° with respect to the closure plane, is reached.

The articulation of the lenticular plug 4 with respect to the ring 1 is furthermore carried out with the help of two pivots 7, preferably parabolic in shape, which are housed in grooves 8 operatively formed in the plug 4 and identical in shape.

The pivots 7 and the grooves 8, as well as the end zones 5 and 6 of the steps 2 and 3 of the ring 1, are so positioned that the axis of articulation of the plug is parallel to the minor axis thereof, dividing its surface into two parts, one of which has a magnitude or size approximately twice that of the other.

It can be deduced from the aforegoing that the cardiac prosthesis of the invention comprises, generally, a butterfly type valve, the plug of which has an oval shape and the axis of articulation of which is offcentered.

From a functional point of view there are two types of prosthesis, a mitral and an aortic, in each one of which two steps, i.e. a systole and a diastole, are established.

In the aortic variety and in the systole step, that is to say, when the left ventricle contracts and discharges blood towards the aorta, the flow of blood exerts a pressure on the widest section of the lenticular plug, determined by its spin axis, thus obtaining the aperture thereof in the aortic light, within a very wide angle with respect to the horizontal or closure position.

This aperture angle of the lenticular plug 4 is determined, besides by the pressure of the flow of blood, by the end zones 5 and 6 of the steps 2 and 3 with which the ring valve is provided in its inner surface, so that the mentioned plug 4 abuts, in its aperture position, against both sides of the axis of articulation thereof.

When the left ventricle has eliminated its blood content under pressure, since the pressure is removed, the lenticular plug 4 descends again towards its initial position, with the help of the blood of the aorta which, at this moment, presents its diastolic pressure. Thus, a perfect closure of the plug is obtained, since the plug is seated on the steps of the ring 1, this closure being perfectly ensured inasmuch as the aortic pressure, with respect to the closure, acts positively on two-thirds of the surface of the plug, while only one-third of the surface of the plug acts against the aortic pressure.

Thus, in this aortic variety and at the time of the diastole, a perfect closure of the lenticular plug 4 on the ring 1 is obtained, since the blood pressure of the flow coming from the left ventricle disappears, at which moment, due to the action-reaction principle and due to the effect of the aortic-diastolic pressure, the lenticular plug 4 descends or returns until it abuts against the steps of the ring.

With respect to the mitral variety, and as is clear, the structure of the valve is exactly maintained, with the only exception that the prosthesis is mounted inversely to that of the aortic position.

During the auricular systole, in this mitral variety, that is to say, when the auricular pressure is greater than the diastolic pressure of the left ventricle, the lenticular plug 4 of the prosthesis is open, proportioning an ample flow of blood from the left auricle to the left ventricle.

On the other hand, the auricular diastole is determined by the closure of the lenticular plug 4 in turn determined mainly by the increase in intraventricular tension, that is to say, by the isometric contraction prior to the discharge of blood towards the aorta.

In any one of the two varieties, there is obtained a valve which offers a perfect closure and a practically diaphanous aperture, thereby permitting a maximum flow of blood and thus resulting in a maximum yield in cardiac capacity.

I claim:

1. A metallic cardiac valve prosthesis device having both aortic and mitral application and the purpose of which is to provide an ample, highly physiological and laminar flow of blood, said device comprising:
   - a valve body in the form of a single and integral ring-shaped member having an oval-shaped inner periphery;
   - said ring-shaped member having formed therein first and second recesses respectively defining first and second substantially planar steps, said first recess opening toward a first axial end of said ring-shaped member, said second recess opening toward a second axial end of said ring-shaped member, said first recess extending along a first circumferential portion of said inner periphery, said second recess extending along a second circumferential portion of said inner periphery, and said second circumferential portion being greater than said first circumferential portion;
   - said first and second recesses having adjacent first ends defined by a pair of respective first end faces positioned adjacent to each other, and said first and second recesses having adjacent second ends defined by a pair of respective second end faces positioned adjacent to each other;
   - said ring-shaped member having integrally formed therewith first and second pivots extending inwardly from said ring-shaped member at positions respectively adjacent said pairs of first and second end faces;
   - a venticular plug in the form of an oval-shaped flat member having formed in the periphery thereof first and second spaced inwardly extending grooves;
   - said flat member being positioned such that said first and second pivots pivotally extend into said first and second grooves, respectively, such that said flat member pivots with respect to said ring-shaped member, between closed and opened positions, about an imaginary pivot axis extending through said pivots and grooves and substantially parallel to and spaced from the minor axis of the oval shape of said flat member;
   - said first and second planar steps being in planes spaced from each other axially of said ring-shaped member by a distance substantially equal to the thickness of said flat member, and said flat member having opposite substantially planar first and second surfaces respectively contacting said first and second planar steps when said flat member is in said closed position;
   - said first and second end faces being substantially planar and abutting said opposite surfaces of said flat member when said flat member is in said opened position; and
   - said first end faces being spaced from each other and said second end faces being spaced from each other by amounts sufficient to enable said flat member, when in said opened position, to extend at an angle of from 80° to 85° with respect to the position of said flat member when in said closed position.

2. A device as claimed in claim 1, wherein said ring-shaped member has a circular-shaped outer periphery.

3. A device as claimed in claim 1, wherein said imaginary pivot axis divides the area of said flat member into first and second portions containing approximately one-third and two-thirds, respectively, of said area.

4. A device as claimed in claim 1, wherein said pivots have a parabolic configuration.

* * * * *